US008911731B2

(12) United States Patent
Mercken et al.

(10) Patent No.: US 8,911,731 B2
(45) Date of Patent: Dec. 16, 2014

(54) MONOCLONAL ANTIBODIES SPECIFIC FOR BETA-AMYLOID X-37 AND USES THEREOF

(75) Inventors: Marc Hubert Mercken, Beerse (BE); Marianne Borgers, Balen (BE); Marc Maria Pierre Pelagie Vandermeeren, Beerse (BE); Bianca Julia J Van Broeck, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/233,068

(22) PCT Filed: Jul. 6, 2012

(86) PCT No.: PCT/EP2012/063213
§ 371 (c)(1),
(2), (4) Date: Jan. 15, 2014

(87) PCT Pub. No.: WO2013/010812
PCT Pub. Date: Jan. 24, 2013

(65) Prior Publication Data
US 2014/0154715 A1    Jun. 5, 2014

(30) Foreign Application Priority Data

Jul. 15, 2011   (EP) .................................. 11174224

(51) Int. Cl.
| A61K 39/395 | (2006.01) |
| C07K 14/47 | (2006.01) |
| A61K 48/00 | (2006.01) |
| A61K 38/10 | (2006.01) |
| C07K 16/18 | (2006.01) |
| G01N 33/577 | (2006.01) |

(52) U.S. Cl.
CPC .............. *G01N 33/577* (2013.01); *C07K 16/18* (2013.01)
USPC ..... 424/139.1; 514/18.1; 514/17.7; 514/17.8; 435/70.21; 435/7.9; 435/7.94; 435/188; 435/7.92; 424/172.1; 424/142.1; 424/141.1; 530/391.3; 530/391.1; 530/328

(58) Field of Classification Search
None
See application file for complete search history.

(56) References Cited

U.S. PATENT DOCUMENTS

| 2003/0073655 | A1* | 4/2003 | Chain .............................. 514/44 |
| 2007/0010503 | A1* | 1/2007 | Findeis et al. ................ 514/172 |
| 2011/0044985 | A1* | 2/2011 | Rosenthal et al. ......... 424/139.1 |

FOREIGN PATENT DOCUMENTS

WO   WO 2011/006903   1/2011

OTHER PUBLICATIONS

McLaurin et al., Therapeutically effective antibodies against amyloid-β peptide target amyloid-β residues 4-10 and inhibit cytotoxicity and fibrillogenesis. Nature Medicine • vol. 8 • No. 11 • Nov. 2002, 1263-1269.*

(Continued)

*Primary Examiner* — Gregory S Emch
*Assistant Examiner* — Aurora M Fontainhas
(74) *Attorney, Agent, or Firm* — Hal B. Woodrow

(57) ABSTRACT

The present invention provides monoclonal antibodies which specifically recognize the shorter Aβ peptides obtained after cleavage of the APP protein mediated by γ-secretase, i.e. the Aβ-peptide fragments Aβ1-37, Aβ3-37, Aβ3p-37, Aβ1-37 and Aβ11p-37, and other like fragments ending at the $37^{th}$ amino acid of APP, hereinafter also referred to as the Aβx-37 peptides. It further provides hybridoma cells producing the monoclonal antibodies as well as methods for producing the antibodies and the hybridoma cells; and an immunoassay for an Aβx-37 peptide by a competitive method or a sandwich method using the antibody of the present invention; and methods for measuring the level of Aβx-37 peptides in a sample, such as a biological sample.

7 Claims, 3 Drawing Sheets

Aβ levels

(56) References Cited

OTHER PUBLICATIONS

International Search Report for PCT/EP2012/063213 dated Dec. 3, 2012.
El Mouedden et al., J. of Neuroscience Methods, vol. 145, p. 97-105 (2005).
Hoglund et al., Neurodegenerative diseases, vol. 5, p. 268-276, 2008.
Kohler et al. Nature, 256, 495-497 (1975).
Kohler et al., Eur. J. Immunol., 6, 292-295 (1976).
Mercken, M. et al., Neurobiol Aging 21, S41 (2000).
Merrifield, R.B., J. Am. Chem. Soc. 85:2149-2156 (1963).
Saido et al., Neuroscience Letters, vol. 215, p. 173-176 (1996).
Schieb et al., J. of Biol Chem, vol. 286, No. 39, p. 33747-33758 (2011).
Takami et al., J Neurosci. (Oct. 14, 2009); 29(41):13042-13052.
Wiltfang et al., J. of Neurochem, vol. 81, p. 481-496 (2002).

* cited by examiner

MONOCLONAL ANTIBODIES SPECIFIC FOR BETA-AMYLOID X-37 AND USES THEREOF

CROSS REFERENCE TO RELATED APPLICATIONS

This application is the national stage of PCT Application No. PCT/EP2012/063213, filed Jul. 6, 2012, which claims priority from European Patent Application No. 11174224, filed Jul. 15, 2011, the entire disclosures of which are hereby incorporated in their entirety.

The present invention relates to new antibodies specific for β-amyloid peptides, their use as diagnostics, biomarkers, or therapeutic agents. More in particular, the present invention describes antibodies specific for Aβx-37 fragments of β-amyloid peptides.

The present invention relates generally to methods and compositions for monitoring the processing of β-amyloid precursor protein. More particularly, the present invention relates to the use of such methods and compositions for the diagnosis, prognosis and monitoring response to therapy of Alzheimer's disease and other β-amyloid peptide related diseases as well as to the use of the disclosed antibodies in passive immunization as a method for treatment of Alzheimer's disease and other β-amyloid peptide related diseases.

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in ethnic groups worldwide and presents a major present and future public health problem. The disease is currently estimated to affect about two to three million individuals in the United States alone. AD is at present incurable. No treatment that effectively prevents AD or reverses its symptoms and course is currently known. The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restricted anatomical distribution are also found in the brains of most aged humans who do not have clinical AD. Amyloid plaques and amyloid angiopathy also characterize the brains of individuals with Trisomy 21 (Down's Syndrome), Diffuse Lewy Body Disease and Hereditary Cerebral Haemorrhage with Amyloidosis of the Dutch-Type (HCHWA-D).

A major constituent of amyloid plaques are a variety amyloid-beta (Aβ) peptides which are produced by cleavage of the β-amyloid precursor protein (APP). APP is a type I transmembrane protein, which undergoes proteolytic processing by several so-called secretase proteins. While in the past there was significant scientific debate over whether the plaques and tangles are a cause or are merely the result of Alzheimer's disease, recent discoveries indicate that amyloid plaque is a causative precursor or factor. In particular, it has been discovered that the production of Aβ peptides can result from mutations in the gene encoding amyloid precursor protein, a protein which when normally processed will not produce the Aβ peptides. The identification of mutations in the amyloid precursor protein gene which cause familial, early onset Alzheimer's disease is the strongest evidence that amyloid metabolism is the central event in the pathogenic process underlying the disease. Aβ is currently regarded as the most important diagnostic parameter.

Takami et al. (γ-secretase: successive tripeptide and tetrapeptide release from the transmembrane domain of β-carboxyl terminal fragment, J Neurosci. (Oct. 14, 2009); 29(41): 13042-13052) gives an overview of β-carboxyl terminal fragment (βCTF) processing. Aβ is believed to be produced by cleavage of βCTF in two long Aβs, $A\beta_{48}$ and $A\beta_{49}$. These are processed further by removal of three or four residues at each step to produce $A\beta_{42}$ and $A\beta_{40}$. $A\beta_{49}$ is converted to $A\beta_{43/40}$ by successively releasing two or three tripeptides, while $A\beta_{48}$ is converted to $A\beta_{42/38}$ by successively releasing two tripeptides and a further tetrapeptide.

In pathological situations, and when using disease-modifying agents, other fragments are generated.

Despite the progress which has been made in understanding the underlying mechanisms of AD and other Aβ-related diseases, there remains a need to develop methods and compositions for diagnosis and treatment of the disease(s). Thus, the ability to monitor cellular processing of the amyloid precursor protein would be of significant value in the diagnosis, prognosis, and therapeutic supervision of Alzheimer's disease. In particular, it would be desirable to identify minimally invasive reproducible procedures for screening and evaluating detectable diagnostic markers in readily obtainable patient samples, such as serum, cerebrospinal fluid (CSF), and the like. Polyclonal antibodies such as the ones described by Said T. C., et al., Neuroscience Letters 215 (1996); 173-176 are useful to detect the different Aβ-peptides in biological samples but given the fact that each batch of polyclonal antibodies is different, these antibodies do not provide the tools to perform reproducible procedures for screening and evaluating detectable diagnostic markers in readily obtainable patient samples. In addition, the non-specific binding using polyclonal antibodies, is typically higher and the accuracy in Western blotting is typically lower.

A number of potential diagnostic markers for Alzheimer's disease have been proposed. Of particular interest to the present invention are the fragments of the Aβ precursor protein obtained after beta-carboxyl terminal fragment processing of the APP protein. These markers should be useful by themselves and/or in combination with other diagnostic markers and procedures. Preferably, the diagnostic markers would be detectable in body fluids, such as CSF, blood, plasma, serum, urine, tissue, and the like, so that minimally invasive diagnostic procedures can be utilized. Also, there is a need for biomarkers for monitoring disease and/or treatment progression, both for use in development of new treatments as in e.g. clinical trial monitoring and the like, or in current treatments.

Specific assays for Aβx-37 detection should be capable of detecting Aβx-37 in fluid samples at very low concentrations in a reproducible and consistent manner as well as distinguishing between Aβx-37 peptides and other fragments of APP, which may be present in the sample.

SUMMARY OF THE INVENTION

The present invention provides monoclonal antibodies which specifically recognize the shorter Aβ peptides obtained after cleavage of the APP protein mediated by γ-secretase, i.e. the Aβ-peptide fragments Aβ1-37, Aβ3-37, Aβ3p-37, Aβ11-37 and Aβ11p-37, and other like fragments ending at the $37^{th}$ amino acid of APP, hereinafter also referred to as the Aβx-37 peptides. It further provides hybridoma cells producing the monoclonal antibodies as well as methods for producing the antibodies and the hybridoma cells; and an immunoassay for an Aβx-37 peptide by a competitive method or a sandwich method using the antibody of the present invention; and methods for measuring the level of Aβx-37 peptides in a sample, such as a biological sample.

In particular, the present invention provides monoclonal antibodies prepared using the polypeptide H2N-CAI IGL MVG-COOH as immunogen. Said antibodies specifically react with the Aβx-37 peptides without cross reactivity for other APP fragments and accordingly, are useful in an immunoassay to assess the role of Aβx-37 in the pathogenesis of Alzheimer's disease.

In a more specific embodiment the monoclonal antibodies are reactive to the polypeptide CAIIGLMVG as immunogen and expressed by the hybridoma JRD/Ab37/3 sc11 or JRD/Ab37/4 sc11 deposited at the Belgian Coordinated Collection of Microorganisms on Feb. 1, 2011 with accession numbers LMBP 8062CB and LMBP 8063CB respectively, or the hybridoma JRD/Ab37/10 sc11 deposited at the Belgian Coordinated Collections of Microorganisms on Mar. 30, 2011 with accession number LMBP 8064CB. It is thus a further embodiment of the present invention to provide the aforementioned hybridoma cells expressing the monoclonal antibodies according to the invention.

In a further aspect of the present invention the antibodies according to the invention are used in conventional immunological techniques for the detection of Aβx-37 peptides wherever it may occur, including biological samples for the monitoring of β-amyloid-related diseases and conditioned media from cell culture for monitoring the intracellular processing of APP. Suitable immunological techniques are well known to those skilled in the art and include for example, ELISA, Western Blot analysis, competitive or sandwich immunoassays and the like, as is otherwise well known they all depend on the formation of an antigen-antibody immune complex wherein for the purpose of the assay, the antibody can be detectable labeled with, e.g. radio, enzyme or fluorescent labels or it can be immobilized on insoluble carriers.

DETAILED DESCRIPTION

Figure 1:
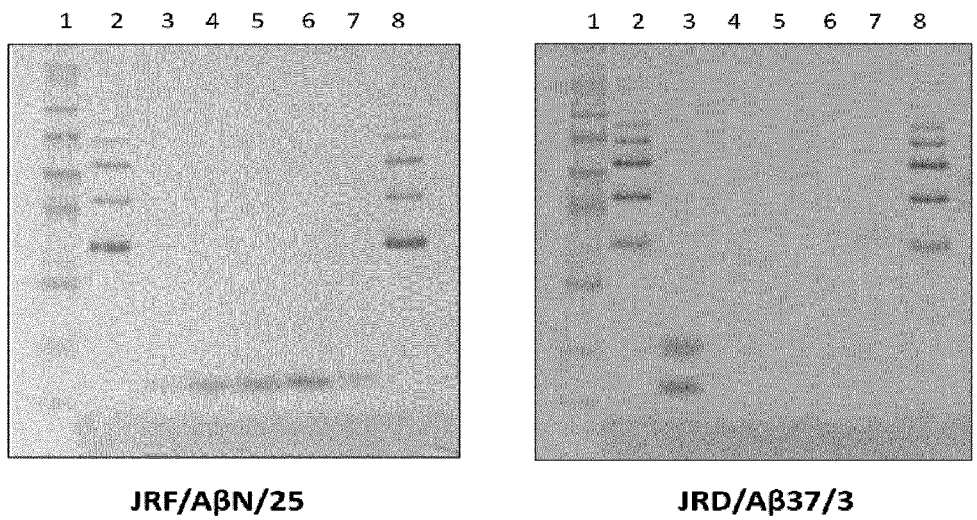
FIG. 1 illustrates the specificity of the anti-Aβ37 antibody produced by the JRD/Ab37/3 hybridoma cells.

The present invention provides monoclonal antibodies which specifically recognize the shorter Aβ peptides obtained after cleavage of the APP protein by βCTF processing. The antibodies of the invention have specificity to one or more epitopes present on Aβx-37 peptides of human Aβ or on Aβx-37 peptides of mouse Aβ.

In particular, the present invention provides monoclonal antibodies prepared using peptides consisting of H₂N-CAI-IGLMVG-COOH (SEQ ID NO: 1) as immunogens.

The aforementioned peptides may be prepared produced by methods known in the art, such as the well-known Merrifield solid-phase synthesis technique where amino acids are sequentially added to a growing chain (Merrifield (1963) J. Am. Chem. Soc. 85:2149-2156). The amino acids sequences may be based on the sequence of the Aβ fragments seth forth above or may utilize naturally occurring or engineered mutant sequences. For use as immunogen, the peptides thus obtained may be used by itself or may be conjugated to a suitable immunoactivating natural or synthetic carrier, such as maleimide activated serum albumin of mammals such as bovine, rabbit, and human, thyroglobulin of mammals such as bovine, rabbit, human and sheep, and keyhole limpet hemocyanin (KLH) or other suitable protein carriers such as the synthetic polymer carriers including styrene polymers, acrylic polymers, vinyl polymers and propylene polymers. Further detailed descriptions of immunization can be found in the examples.

Once a sufficient amount of the immunogen has been obtained, polyclonal antibodies specific for the Aβx-37 peptides may be produced in various ways using techniques including in vitro or in vivo techniques. In vitro techniques involve exposure of lymphocytes to the immunogens, while in vivo techniques require the injection of the immunogens into a suitable vertebrate host. Suitable vertebrate hosts are non-human, including mice, rats, rabbits, sheep, goats and the like. Immunogens are injected into the animal according to a predetermined schedule, and the animals are periodically bled with successive bleeds having improved titer and specificity. The injections may be made intramuscularly, intraperitoneally, subcutaneously, or the like and an adjuvant, such as Freund's complete adjuvant or Freund's incomplete adjuvant may be given to enhance antibody producing ability. Methods for screening the serum titer levels typically include standard ELISA or RIA assays. For example in an ELISA screening format the serum is added to a solid phase (for example the bottom of a microplate) which is coated with either the Aβx-37 peptide or the Aβx-37 peptide coupled to a carrier (such as BSA), and then, adding an anti-immunoglobulin antibody (for example when the immunization is performed in mice, an anti-mouse immunoglobulin antibody is used, e.g. sheep-anti-mouse immunoglobulin (Ig)) conjugated with a detectable label such as an enzyme, preferably horseradish peroxidase, or a radioactive isotope such as $^{125}I$.

If desired, monoclonal antibodies can be prepared from the vertebrate hosts, such as a mouse, hyperimmunized with the desired immunogen by the method just described, using techniques well understood by those having ordinary skill in the art. Conveniently, a vertebrate host showing a high titer antibody is selected from the animals immunized with the desired immunogen. Typically 2 to 5 days, preferably 4 days after the final immunization, the spleen or lymph nodes are collected therefrom, and antibody-producing cells contained therein immortalized. The manner of immortalization is not critical. Presently, the most common technique is fusion with a myeloma cell fusion partner. The fusing procedure can be conducted according to methods known in the art, for example, the method of Kohler and Milstein (Nature, 256, 495-497 (1975)). Other techniques include EBV transformation, transformation with bare DNA e.g. oncogenes, retroviruses, etc., or any other method which provides for stable maintenance of the cell line and production of monoclonal antibodies. Fusion accelerators, including polyethylene glycol (PEG) and Sendai virus, may be used. In particular PEG is preferably used. Examples of the myeloma cells include NS-1, P3U1, SP2/0 and AP-1, SP2/0 cells are preferably used.

Hybridomas producing monoclonal antibodies specific for epitopes which are found on the C-terminal of Aβx-37 peptides are most effectively produced by first immunizing an animal from which hybridomas can be produced such as, for example a Balb/c mouse, with initial intraperitoneally injections of the desired immunogens in Freund's adjuvant, followed by booster injections every two weeks. The subsequent fusion of the isolated spleen can be carried out using any techniques commonly known to those of ordinary skill in the art, preferably using SP2/0 cells by a modified procedure of Kohler and Milstein (Eur. J. Immunol., 6, 292-295 (1976)). The screening of the hybridomas to determine which ones are producing antibodies specific for the Aβx-37 peptides can be done either in a standard ELISA or RIA assay as described hereinbefore. Selection and breeding of the hybridomas producing the desired monoclonal antibodies, is usually conducted in a medium for animals (for example Dulbecco's modified Eagle's medium (DMEM) or Eagle's minimum essential medium (MEM)) supplemented with 10-20% fetal calf serum and other components such as, for example, HAT (hypoxanthine, aminopterin and thymidine), or ESG Hybridoma supplement. Accordingly in an embodiment the present invention provides the hybridoma cells JRD/Ab37/3 sc11 or JRD/Ab37/4 sc11 deposited at the Belgian Coordinated Collection of Microorganisms on Feb. 1, 2011 with accession numbers LMBP 8062CB and LMBP 8063CB respectively, or the hybridoma JRD/Ab37/10 sc11 deposited at the Belgian Coordinated Collections of Microorganisms on Mar. 30, 2011 with accession number LMBP 8064CB.

Separation and purification of the anti-Aβx-37 monoclonal antibodies are carried out similarly to usual separation and purification of polyclonal antibodies such as salt precipitation, alcohol precipitation, isoelectric precipitation, electrophoresis, adsorption and desorption with ion-exchange materials (for example DEAE), ultracentrifugation, gel filtration and specific immunoaffinity separation techniques including antigen-binding solid phases and protein A or protein G affinity chromatography. Suitable protein purification techniques are described in *Methods in Enzymology*, Vol. 182, Deutcher, ed., Academic Press. Inc., San Diego, 1990, the disclosure of which is incorporated herein by reference.

It is thus an object of the invention to provide isolated monoclonal antibodies expressed by the aforementioned hybridoma cells, said antibodies capable of specifically recognising Aβx-37 peptides. Preferably these isolated monoclonal antibodies are expressed by the hybridoma cells JRD/Ab37/3 sc11 or JRD/Ab37/4 sc11 deposited at the Belgian Coordinated Collection of Microorganisms on Feb. 1, 2011 with accession numbers LMBP 8062CB and LMBP 8063CB respectively, or the hybridoma JRD/Ab37/10 sc11 deposited at the Belgian Coordinated Collections of Microorganisms on Mar. 30, 2011 with accession number LMBP 8064CB.

The antibodies according to the invention are used in conventional immunological techniques for the detection of Aβx-37 peptides wherever it may occur, including biological samples for the monitoring of β-amyloid-related diseases and conditioned media from cell culture for monitoring the intracellular processing of APP. Suitable immunological techniques are well known to those skilled in the art and include for example, ELISA, Western Blot analysis, competitive or sandwich immunoassays and the like, as is otherwise well known they all depend on the formation of an antigen-antibody immune complex wherein for the purpose of the assay, the antibody can be detectable labelled with, e.g. radio, enzyme, luminescent or fluorescent labels or it can be immobilized on insoluble carriers. It is thus an object of the invention to provide immunoassays for the determination or detection of Aβx-37 peptides in a sample, the method comprising contacting the sample with an antibody to Aβx-37 peptides according to the invention and determining whether an immune complex is formed between the antibody and the Aβx-37 peptide. These methods can either be performed on tissue samples or body fluid samples and generally comprise obtaining a sample from the body of a subject; contacting said sample with an imaging effective amount of a detectably labelled antibody according to the invention; and detecting the label to establish the presence of Aβx-37 peptides in the sample.

The measuring methods using the antibodies of the present invention are not particularly limited. Any measuring method may be used as long as the amount of antibodies, antigens or the antigens-antibody complexes corresponding to the amount of the antigens, in particular the amount of Aβx-37 peptides in solutions to be measured is detected by chemical or physical means, and calculated from standard curves prepared by the use of standard solutions containing the antigens in known amounts. For example, nephelometry, competitive methods, immunometric methods and sandwich methods are suitably used. With respect to sensitivity and specificity, it is particularly preferred to use sandwich methods described below.

In measuring methods using labelling substances, radioisotopes, enzymes, fluorescent substances, luminous substances, etc. are used as labelling agents. Examples of the radioisotopes include $^{125}$I, $^{131}$I, $^{3}$H and $^{14}$C. Enzymes are usually made detectable by conjugation of an appropriate substrate that, in turn catalyzes a detectable reaction. Examples thereof include, for example, beta-galactosidase, beta-glucosidase, alkaline phosphatase, peroxidase and malate deydrogenase, preferably horseradish peroxidase. The luminous substances include, for example, luminol, luminol derivatives, luciferin, aequorin and luciferase. Further, the avidin-biotin systems can also be used for labelling the antibodies and immunogens of the present invention.

When the immunogens or antibodies are insolubilized, either physical adsorption or chemical binding usually used for insolubilization or fixation of proteins or enzymes may be employed. Examples of the carriers include insoluble polysaccharides such as agarose, dextran, and cellulose, synthetic resins such as polystyrene, polyacrylamide and silicone polymers, and glass.

In the sandwich methods, the test solutions are reacted with the insolubilized anti-Aβx-37 peptide capture antibodies (the first reaction), further, the labeled anti-Aβx-37 peptide detection antibodies are reacted (the second reaction), and then, the activity of the labelling agents on the insolubilized carriers is assayed, whereby the amount of the Aβx-37 peptides in the test solutions can be determined. The first reaction and the second reaction may be conducted simultaneously or sequentially.

In a further embodiment for diagnosing β-amyloid-related diseases a biological sample including tissue, body fluids, such as CSF, blood, plasma, serum, urine, and the like, is contained and contacted with a suitable amount of first antibody to produce an immune complex. The contact typically involves adding the sample to a solid matrix coated with the first antibody. The complex which results from contacting the sample with the first antibody is separated from the sample by elution. However, other methods of recovery may be employed. The recovered complex is contacted with at least one second antibody directed to an antigenic determinant on the antigen and capable of binding the antigen in the complex. The antigenic determinant to which the second antibody is directed may be the same one as to which the first antibody is directed due to the multi-epitopic nature of the antigenic entity. Either the first or the second antibody may be made detectable using any of the labels described above. In a specific embodiment, the second antibody is made detectable. The presence of the detectable antibody bound to the complex consisting of antigen bound to the first and second antibody may be readily detected using art-known techniques. By comparing the results obtained in the biological sample with those obtained on a control sample, the presence of altered Aβx-37 peptide levels may be determined.

It is accordingly, an object of the present invention to provide a sandwich assay wherein the first antibody coated to a solid matrix, hereinafter referred to as the coating antibody, consists of an antibody that recognizes the Aβx-37 peptides and the second antibody, which is made detectable, specifically recognizes the N-terminus of Aβ peptides. Advantageously, the coating antibody recognizes the human Aβx-37 peptides, in a more specific embodiment the coating antibody is selected from the group consisting of the monoclonal antibodies JRF/Ab37/3, JRF/Ab37/4 and JRF/Ab37/10 that specifically recognize Aβx-37. In an advantageous embodiment the second antibody is the monoclonal antibody expressed by the hybridoma cells JRF/Aβ/N25. It is also an object of the invention to provide a sandwich assay to determine the ratio of Aβx-37 peptides to Aβ38, Aβ40 or Aβ42 peptides. In this embodiment an additional second antibody is used that recognizes Aβ38, Aβ40 or Aβ42 peptides, but which shows no cross reactivity for Aβx-37 peptides as well. It is accordingly an object of the present invention to provide a sandwich assay wherein the coating antibody consists of an antibody that specifically recognizes the Aβx-37 peptides, but which shows no cross reactivity for the full length Aβ40 and Aβ42 peptides, the monoclonal antibodies JRF/Ab37/3, JRF/Ab37/4 and JRF/Ab37/10.

The monoclonal antibodies of the present invention can also be used in assay systems other than the sandwich methods, for example, competitive methods and nephelometry. In the competitive methods, antigens in test solutions and labeled immunogens are competitively reacted with the antibodies, followed by separation of the unreacted labeled immunogens (F) from the labeled imunogens (B) bound to the antibodies (B/F separation). Then, the labeled amount of either B or F is measured to determine the amount of immunogen in the test solution. These reaction methods include liquid phase methods in which soluble antibodies are used as the antibodies and polyethylene glycol and the second antibodies to the above mentioned antibodies are used for B/F separation, and solidifying methods in which solidified antibodies are used as the first antibodies, or soluble antibodies are used as the first antibodies and solidified antibodies are used as the second antibodies.

In nephelometry, the amount of the insoluble precipitates produced as a result of antibody-antigen reaction in gels or solutions is measured. Even when the amount of antigens is slight, and the precipitates are obtained only in small amounts, laser nephelometry using laser scattering is suitably used.

In a further aspect, the invention is directed to a method for monitoring treatment with the antibodies of the invention. More in particular, the antibodies and detection methods of the present invention can be used to monitor the effects of diverse disease-modifying drugs in Alzheimer's disease patients. Examples of such disease-modifying drugs include but is not limited to so-called GSM (gamma secretase modulator), GSI (gamma secretase inhibitor) or BACE inhibitor compounds.

The present invention further provides kits that can be used in the above mentioned methods. In one embodiment, a kit comprises an antibody of the invention, preferably a purified antibody, more preferably a monoclonal antibody, even more preferably the isolated monoclonal antibodies expressed by the hybridoma cells JRD/Ab37/3 sc11 or JRD/Ab37/4 sc11 deposited at the Belgian coordinated collection of microorganisms on Feb. 1, 2011 with accession numbers LMBP 8062CB and LMBP 8063CB respectively, or the hybridoma JRD/Ab37/10 sc11 deposited at the Belgian Coordinated Collections of Microorganisms on Mar. 30, 2011 with accession number LMBP 8064CB in one or more containers. In a specific embodiment, the kits of the present invention contain a substantially isolated polypeptide comprising an epitope which is specifically immunoreactive with an antibody included in the kit. In a further embodiment this epitope is present on the C-terminal of Aβx-37 peptides. Preferably, the kits of the present invention are arranged for use in a sandwich assay and further comprise a coating antibody which does not specifically react with the polypeptide of interest, in a specific embodiment this coating antibody recognizes Aβ1-37 peptides such as human Aβ1-37 peptides and Aβ1-38, Aβ3-40 or Aβ1-42 such as human Aβ1-38, Aβ1-40 or Aβ1-42. In a specific embodiment the coating antibody is JRF/Aβ/N25. In alternative sandwich assay according to the invention, the kits will comprise a coating antibody that specifically recognizes the Aβx-37 peptides, such as the human Aβx-37 peptides. In a more specific embodiment the kit will comprise the isolated monoclonal antibodies expressed by the hybridoma cells JRD/Ab37/3 sc11 or JRD/Ab37/4 sc11 deposited at the Belgian Coordinated Collection of Microorganisms on Feb. 1, 2011 with accession numbers LMBP 8062CB and LMBP 8063CB respectively, or the hybridoma JRD/Ab37/10 sc11 deposited at the Belgian Coordinated Collections of Microorganisms on Mar. 30, 2011 with accession number LMBP 8064CB as coating antibodies, and the monoclonal antibodies JRF/Aβ/N25 as further antibody, the latter being conjugated to a detectable label.

In another specific embodiment, the kits of the present invention contain means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In particular the kit contains means to detect the binding of an antibody to Aβx-37 peptides, preferably to detect binding with an epitope is present on the C-terminal of Aβx-37 peptides. In the aforementioned sandwich assays, the antibody conjugated to a detectable substrate will not be the coating antibody. In an additional embodiment, the invention includes a diagnostic kit for use in screening biological samples including tissue, body fluids, such as CSF, blood, plasma, serum, urine, and the like. Said biological sample containing Aβx-37 peptides. The diagnostic kit includes a substantially isolated antibody specifically immunoreactive with Aβx-37 peptides, in particular with an epitope is present on the C-terminal of Aβx-37 peptides, and means for detecting the binding of the antibody to the immunogen. In one embodiment, the antibody is attached to a solid support. In a specific embodiment, the antibody may be a monoclonal antibody, in particular the monoclonal antibodies expressed by the hybridoma cells JRD/Ab37/3 sc11 or JRD/Ab37/4 sc11 deposited at the Belgian Coordinated Collection of Microorganisms on Feb. 1, 2011 with accession numbers LMBP 8062CB and LMBP 8063CB respectively, or the hybridoma JRD/Ab37/10 sc11 deposited at the Belgian Coordinated Collections of Microorganisms on Mar. 30, 2011 with accession number LMBP 8064CB.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound antibodies according to the invention, and a reporter-labeled antibody for detecting the binding of the antibody to the immunogen.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXPERIMENTAL

Material and Methods

Generation of Monoclonal Antibodies

2 Balb/c mice were primed with H2N-CAI IGL MVG-COOH (SEQ ID NO 01) in complete Freund's adjuvant. The peptides were prepared for immunization by coupling via a COOH-terminal cystein residue to maleimide activated mc(*Megathura crenulata*) KLH, or to Maleimide Activated Bovine Serum Albumin, using commercially available kits such as the Imject Maleimide Activated mcKLH/BSA kit of Pierce, according to the manufacturer's instructions (Pierce, Rockford, Ill.). Mice were boosted every two weeks with 100 µg or 200 µg KLH-coupled peptide, first in Complete and subsequently in Incomplete Freund's adjuvant.

The mouse showing the highest serum titer was selected for fusion, while the spleen of the second mouse was isolated and frozen in liquid nitrogen. On day 4 before fusion or spleen extraction, all mice were boosted intraperitoneally with 100 µg of H2N-CAI IGL MVG-COOH coupled to mcKLH in saline. Mouse spleen cells were fused with SP2/0 cells by a modified procedure of Kohler and Milstein (Eur. J. Immunol., 6, 292-295 (1976)). The hybridomas were seeded in 30×96-well plates and screened after 10 days in a direct ELISA on 0.5 µg/well non-coupled peptide Aβ1-37 (AnaSpec, Fremont, USA). Positive cells were tested for cross-reactivity on 0.5 µg/ml coated Aβ1-37, Aβ1-38 and Aβ1-39 peptide (AnaSpec, Fremont, USA) and were immediately subcloned. Positive clones were frozen in liquid nitrogen.

All hybridomas were grown in Dulbecco's modified Eagle's medium supplemented with 10% foetal calf serum (Hyclone, Europe), Hybridoma Fusion Cloning Supplement (2%) (Roche, Brussels, Belgium) 2% HT (Sigma, USA), 1 mM sodium pyruvate, 2 mM L-glutamine and penicillin (100 U/ml) and Streptomycin (50 mg/ml). All products were commercially available and purchased from Life-Technologies (Paisley, U.K.). Cells were incubated in a humidified 8% CO2 air incubator.

Direct ELISA for Antibody Selection

The screening ELISA used for the detection of anti-Aβx-37 antibodies was a direct ELISA with 0.5 µg/ml free human Aβ1-37 peptide coated overnight at 4° C. in NUNC Maxisorp (Life Technologies) flat-bottom high-binding 96-well microtiter plates in 50 µl/well coating buffer (10 mM Tris, 10 mM NaCl, and 10 mM NaN3, pH 8.5). The next day, the plates were coated with 75 µl/well of 0.1% casein in PBS for 60 min at room temperature to reduce non-specific binding. Next, 50 µl hybridoma supernatant was added and incubated for 1 h at 37° C. After washing, the bound monoclonal antibodies were detected with 50 µl/well of Sheep-anti-mouse IgG conjugated with horseradish peroxidase for 1 hr at 37° C. (Amersham-Pharmacia Biotech). Both reagents were diluted in 0.1% Casein/PBS. The plates were washed and 50 µl of a solution of 0.42 mM 3,5,3',5'-tetramethyl-benzidine, 0.003% (vol/vol) H2O2 in 100 mM citric acid and 100 mM disodium hydrogen phosphate (pH 4.3) was added as the substrate. The reaction was allowed to proceed for maximum 15 min on a plate shaker at room temperature, after which the colour development was stopped with 2 N $H_2SO_4$, 50 µl/well, and plates were read on a microtiter plate reader at 450 nm (Thermomax, Molecular Devices). The cross-reactivity of the selected monoclonal antibodies with full-size human free Aβ1-38 and Aβ1-39 peptide was tested in a direct ELISA, identical to the screening assay.

Sandwich ELISA for Selectivity Testing

Standards of human Aβ1-37, Aβ1-38, Aβ1-39, Aβ1-40 and Aβ1-42 were dissolved in dimethylsulphoxide (DMSO) at 0.1 mg/mL and stored at −80° C. For use in ELISA, peptides were further diluted in 0.1% casein in PBS down to 1 pg/mL. Ninety six-well-plates (half-area black plates, Costar) were coated overnight at 4° C. with monoclonal antibodies at a concentration of 1.5 µg/mL in coating buffer. JRD/Aβ37/3 was used as capture antibody for Aβ1-37. The next day, plates were washed and blocked with 0.1% casein in PBS for 1-4 hours at room temperature. Standards and undiluted samples were incubated overnight at 4° C. together with HRPO-labeled secondary antibody JRF/Aβ/N25 (antibody that specifically recognizes the N-terminus of full-size human Aβ peptide (Mercken, M. et al., Neurobiol Aging 21, S41 (2000)). After overnight incubation, plates were washed and Aβ1-37 assay was developed with Quantablu substrate (Pierce) according to the manufacturer's recommendations.

Immunoblot—Specificity of $A\beta_{37}$ Monoclonal Antibodies

5 µg of each synthetic peptide ($A\beta_{1-37}$, $A\beta_{1-38}$, $A\beta_{1-39}$, $A\beta_{1-40}$, $A\beta_{1-42}$) was loaded on a NuPAGE® Novex® Bis-Tris 12% gel and blotted on a nitrocellulose membrane by use of an iBlot system (Invitrogen), according to the manufacturer's instructions. Membranes were blocked for 1 hour with Tris-Buffered Saline Tween-20 (TBS-T; 1M Tris, 150 mM NaCl and 0.05% Tween-20, pH8.5) containing non fat dry milk (NFDM) (5% w/v; Biorad) and washed three times in TBS-T. Incubation with the primary antibodies (5 µg/ml) diluted in TBS-T containing NFDM (5% w/v) was overnight at 4° C. Primary antibodies were detected using Sheep-anti-mouse Ig conjugated with HRPO (1:20000 in TBS-T, Amersham Biosciences) via West Dura® enhanced chemiluminescence (Pierce, Thermoscientific). Signals were captured by the Lumi-imaging system (Roche Diagnostic).

Cross-reactivity of the selected $A\beta_{37}$ monoclonal antibodies with human $A\beta_{1-38}$, $A\beta_{1-39}$, $A\beta_{1-40}$ and $A\beta_{1-42}$ synthetic peptides was evaluated by detection with JRD/Aβ37/3 as primary antibody. The detection with JRF/AβN/25 monoclonal antibody was performed to confirm correct loading of the different peptides.

Results are shown in FIG. 1. Lanes were charged as follows:

| 1 | 2 | 3 | 4 | 5 | 6 | 7 | 8 |
|---|---|---|---|---|---|---|---|
| Seeblu | MagicM | Ab37 | Ab38 | Ab39 | Ab40 | Ab42 | MagicM |

Quantification of Aβ1-37 in Dog CSF

12 Beagle dogs were orally dosed with one of two GSM compounds (GSM A: compound 97 and GSM B: compound 157 from WO2011/006903) in Methocel suspension together with a liquid meal. Cerebrospinal fluid (CSF) was collected prior to treatment and at 4, 8, 24 and 48 h after dosing. The liquid meal was 120 ml of a concentrated liquid diet (Convalescence Support®, 1 sachet was dissolved in 112.5 ml warm water) and dosing was done directly before the meal.

Aβ levels in dog were quantified with JRD/Aβ37/3 in a direct ELISA as described above for selectivity testing.

Figure 2:
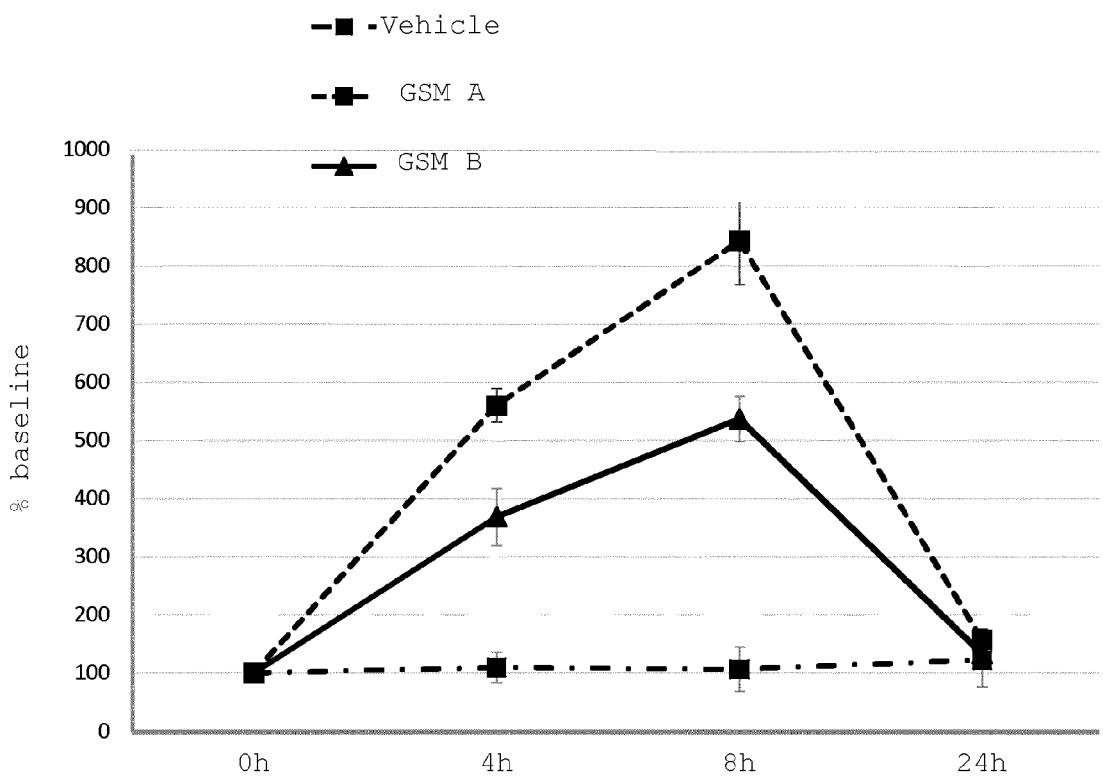
FIGS. 2 and 3 respectively show measurement of increase in Aβ37 in dog and monkey CSF after treatment with respectively GSM (gamma-secretase modulator) A and B for dog and E2012 for monkey.

Results are shown in FIG. 2.

Quantification of Aβ1-37 in Monkey CSF

Seven young cynomolgus monkeys (*Macaca fascicularis*) with surgically implanted cistern magna catheters were treated with single oral doses of GSM E-2012. Cerebrospinal fluid (CSF) and blood was collected prior to treatment (0 h) and at multiple postdose timepoints (0.5, 1, 2, 4, 6, 8, 12, 16, 24, 48 h). Animals were observed daily for clinical signs and body weights were recorded prior to dosing.

Aβ levels in the CSF samples were quantified with an AlphaScreen™ method. Standards of $A\beta_{1-37}$ synthetic peptide was dissolved in DMSO at 0.1 mg/mL and stored at −80° C. For use in the assay, peptides were further diluted in 0.1% casein in PBS with 0.05% Tween-20 down to 10 pg/mL. Unconjugated acceptor beads (PerkinElmer, Little Chalfont, UK) were coupled to monoclonal antibodies following manufacturer's instructions. Antibody JRD/Aβ37/3 was coupled to acceptor beads for use in $A\beta_{1-37}$ assay. JRF/AβN/25 was biotinylated using ChromaLink™ Biotin 354S (SoluLink Biosciences) following manufacturer's instructions.

Standards and prediluted CSF samples (½ dilution) were incubated in 384-well Optiplates for 1 hour at room temperature together with conjugated acceptor beads (12.5 μg/mL) and JRF/AβN/25 biotinylated antibody. Subsequently, streptavidin-labeled donor beads (25 μg/mL; PerkinElmer) were added to the reaction mixture. After an incubation of 30 minutes at room temperature, plates were read on Envision microtiter plate reader (PerkinElmer). Results are shown in FIG. 3.

Figure 3:
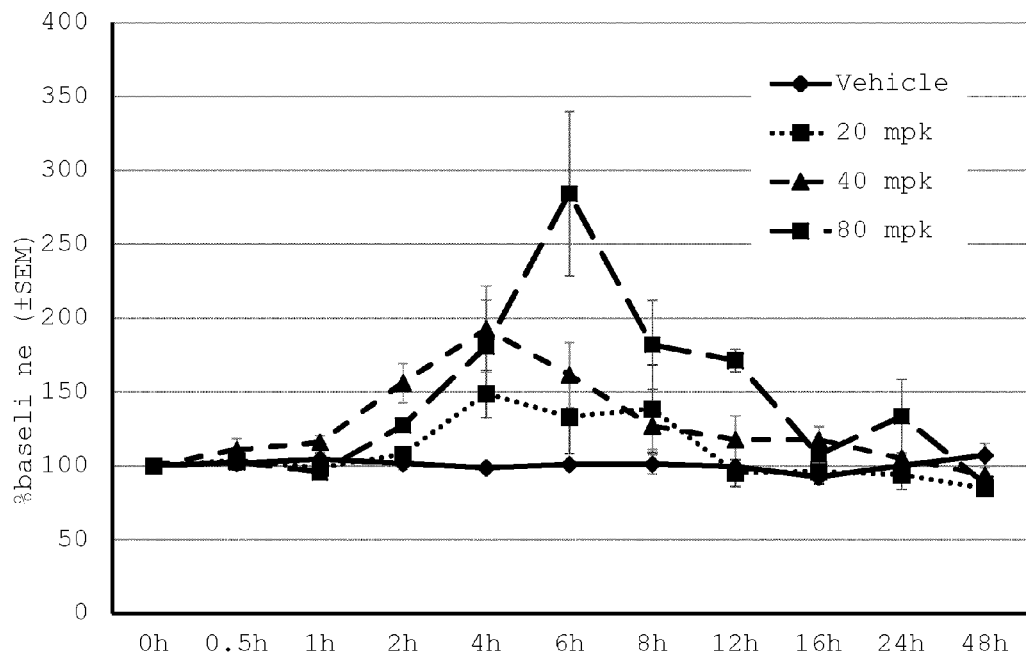

The data as presented in FIGS. 2 and 3 show that quantification of Aβ1-37 peptides can be used as a pharmacodynamic marker to monitor GSM treatment.

Quantification of Aβ1-37 in Human CSF

CFS samples from 9 healthy controls, 6 neurological controls and 9 Alzheimer disease patients were screened for Aβ37, Aβ38, Aβ40 and Aβ42 using MSD Sector instrument SI6000 and MSD Prototype 4-plex plates. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cβ42/26) were coated on MSD 4-plex plates and Sulfo-tag labelled JRF/AβN/25 antibody was used as detector antibody.

Simultaneous specific detection of Abeta37, Abeta38, Abeta40, and Abeta42 was performed using MSD's electrochemiluminescence detection technology. The SULFO-TAG emits light upon electrochemical stimulation initiated at the electrode surface of the 4-plex plates.

Figure 4:
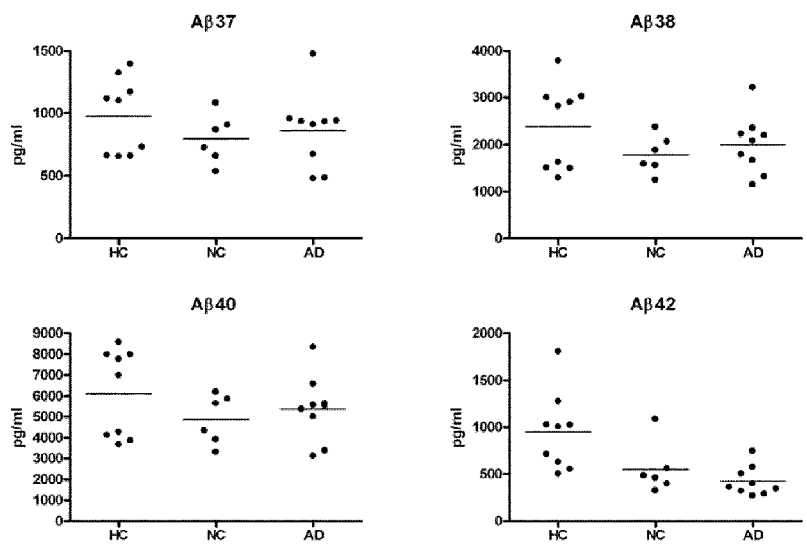
FIG. 4 shows the levels of different Aβ fragments as measured in healthy controls (HC), neurological controls (NC) and Alzheimer's disease patients (AD).

Results are shown in Table 1 and FIG. 4:

TABLE 1

|  |  | Concentration (pg/ml) | | | |
|---|---|---|---|---|---|
|  | ID | Aβ37 | Aβ38 | Aβ40 | Aβ42 |
| Healthy Control | 1 | 653,6501 | 1283,717 | 3847,112 | 501,2267 |
|  | 2 | 660,4071 | 1503,224 | 4098,037 | 551,0089 |
|  | 3 | 1166,451 | 2813,172 | 7749,327 | 1020,566 |
|  | 4 | 728,8013 | 1487,931 | 3657,584 | 627,8834 |
|  | 5 | 1321,41 | 2995,137 | 6976,366 | 1272,656 |
|  | 6 | 1393,55 | 3783,929 | 8570,242 | 1803,956 |
|  | 7 | 656,6728 | 1616,908 | 4245,79 | 712,2321 |
|  | 8 | 1114,129 | 3020,726 | 7984,909 | 1001,475 |
|  | 9 | 1098,714 | 2902,689 | 7981,896 | 1023,682 |
| Neurological Control | 1 | 724,738 | 1874,41 | 5627,762 | 556,9327 |
|  | 2 | 904,0785 | 2054,187 | 5856,235 | 482,1726 |
|  | 3 | 655,5548 | 1556,124 | 4315,03 | 456,8318 |
|  | 4 | 1080,013 | 2368,43 | 6188,724 | 1083,708 |
|  | 5 | 865,9594 | 1581,803 | 3903,329 | 395,0011 |
|  | 6 | 534,8445 | 1242,524 | 3292,696 | 324,8352 |
| AD patients | 1 | 476,4525 | 1140,943 | 3360,445 | 289,5164 |
|  | 2 | 936,4183 | 2345,013 | 5535,373 | 319,7071 |
|  | 3 | 670,7609 | 1657,716 | 4997,462 | 360,6308 |
|  | 4 | 957,4371 | 2192,229 | 6581,381 | 396,8105 |
|  | 5 | 929,3731 | 2079,159 | 5554,406 | 344,065 |
|  | 6 | 932,241 | 1782,768 | 5348,286 | 572,7802 |
|  | 7 | 1474,76 | 3211,914 | 8343,712 | 743,708 |
|  | 8 | 481,5436 | 1315,199 | 3112,098 | 267,7054 |
|  | 9 | 907,7838 | 2224,667 | 5631,433 | 502,2027 |

Figure 5:
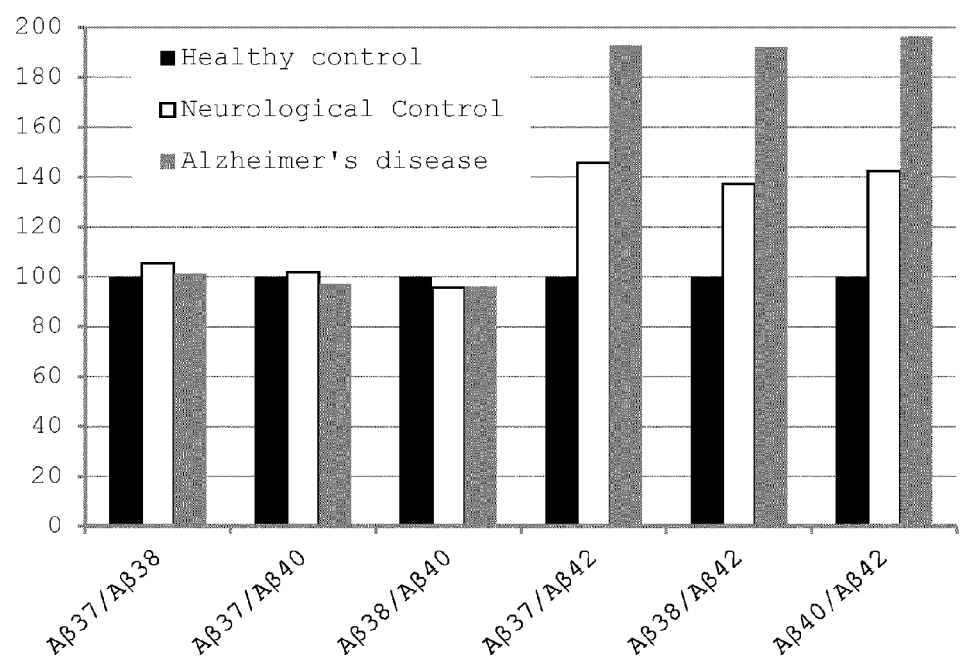
FIG. 5 compares ratios between Aβ fragments as determined in healthy controls (HC), neurological controls (NC) and Alzheimer's disease patients (AD).

Average ratios can be calculated between the relative amounts of Aβ fragments. Results are shown in Table 2 and FIG. 5:

TABLE 2

|  | Ratios (average) | | | | | |
|---|---|---|---|---|---|---|
|  | Aβ38/Aβ40 | Aβ40/Aβ42 | Aβ38/Aβ42 | Aβ37/Aβ38 | Aβ37/Aβ40 | Aβ37/Aβ42 |
| Healthy Control | 0.3849 | 6.7217 | 2.5543 | 0.4240 | 0.1627 | 1.0805 |
| Neurol. Control | 0.3683 | 9.5708 | 3.5079 | 0.4470 | 0.1656 | 1.5745 |
| AD Patients | 0.3709 | 13.2114 | 4.9127 | 0.4291 | 0.1583 | 2.0851 |

The invention claimed is:

1. A monoclonal antibody which specifically recognizes Aβx-37 peptide and is produced by a hybridoma selected from the group consisting of JRD/Ab37/3 sc11 deposited at the Belgian Coordinated Collection of Microorganisms on Feb. 1, 2011 with accession number LMBP 8062CB, JRD/Ab37/4 sc11 deposited at the Belgian Coordinated Collection of Microorganisms on Feb. 1, 2011 with accession number LMBP 8063CB, and JRD/Ab37/10 sc11 deposited at the Belgian Coordinated Collections of Microorganisms on Mar. 30, 2011 with accession number LMBP 8064CB.

2. The monoclonal antibody of claim 1, wherein said Aβx-37 peptide is selected from the group consisting of the Aβ-peptide fragments Aβ1-37, Aβ3-37, Aβ3p-37, Aβ11-37 and Aβ11 p-37.

3. The monoclonal antibody of claim 1, which is detectably labeled.

4. The monoclonal antibody of claim 3, wherein the detectable label is a radiolabel, an enzyme label, a luminescent label or a fluorescent label.

5. The monoclonal antibody of claim 4, which is immobilized on a carrier.

6. A method for the determination or detection of the presence of Aβx-37 peptides in a sample, comprising contacting the sample with the monoclonal antibody of claim 1 and determining whether an immune complex is formed between said monoclonal antibody and said Aβx-37 peptide.

7. The method of claim 6, wherein said sample is selected from the group consisting of a tissue sample and a body fluid sample from a mammal.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: immunogenic peptide

```
<400> SEQUENCE: 1

Cys Ala Ile Ile Gly Leu Met Val Gly
1               5
```